United States Patent [19]

Spencer et al.

[11] Patent Number: 4,975,052
[45] Date of Patent: Dec. 4, 1990

[54] ORTHODONTIC APPLIANCE FOR REDUCING TOOTH ROTATION

[76] Inventors: William Spencer, 4204 Windy Oaks Rd., Louisville, Ky. 40241; Bruce Haskell, 1628 Sutherland Dr., Louisville, Ky. 40205

[21] Appl. No.: 339,791

[22] Filed: Apr. 18, 1989

[51] Int. Cl.⁵ ............................................. A61C 3/00
[52] U.S. Cl. ..................................................... 433/21
[58] Field of Search ..................... 433/21, 24, 20, 22, 433/18, 16

[56] References Cited

U.S. PATENT DOCUMENTS

| | | | |
|---|---|---|---|
| 3,121,953 | 2/1964 | Asher | 433/5 |
| 3,137,941 | 6/1964 | Andrews | 433/5 |
| 3,162,948 | 12/1964 | Gerber | 433/21 |
| 3,256,602 | 6/1966 | Broussard et al. | 433/21 |
| 4,197,643 | 4/1980 | Burstone et al. | 433/20 |
| 4,199,865 | 4/1980 | Cain | 433/21 |
| 4,255,139 | 3/1981 | Ladanyi | 433/21 |
| 4,478,577 | 10/1984 | Warren, Jr. | 433/18 |
| 4,664,626 | 5/1987 | Kesling | 433/16 |

OTHER PUBLICATIONS

Ricketts, R. M., "Development of Retraction Sections", (Part 10), Features of the Bioprogressive Therapy (No. 16) (1974).
Gjessing, P., "Biomechanical Design and Clinical Evaluation of a New Canine-Retraction Spring", Am. J. Orthod. v. 87, No. 5, pp. 353–362, St. Louis, (May, 1985).
Ziegler, P. and Ingervall, B., "A Clinical Study of Maxillary Canine Retraction With a Retraction Spring and With Sliding Mechanics", v. 95, pp. 99–106 (1989).

*Primary Examiner*—Cary E. Stone
*Attorney, Agent, or Firm*—Sheridan, Ross & McIntosh

[57] ABSTRACT

An orthodontic appliance for preventing unwanted rotation of a tooth during its translational movement along a main guide-wire. The appliance is adapted to be held by at least one bracket affixed to a tooth. The appliance includes a main spring assembly for causing, when activated, translational movement of a tooth along the main guide-wire to reduce space between the tooth and another tooth. An auxiliary spring assembly, which is separate and spaced from the main spring assembly, includes a spring and a mesial leg extending from the spring. The auxiliary spring assembly is used to substantially prevent unwanted rotation of the tooth being moved in a lateral direction. Orthodontic wire, which includes an anchoring end, interconnects the auxiliary spring assembly and the main spring assembly. In the preferred embodiment, the mesial leg and spring are connected to a side of the bracket while the anchoring end is connected to another tooth other than the tooth having the bracket to which the auxiliary spring assembly is connected.

18 Claims, 5 Drawing Sheets

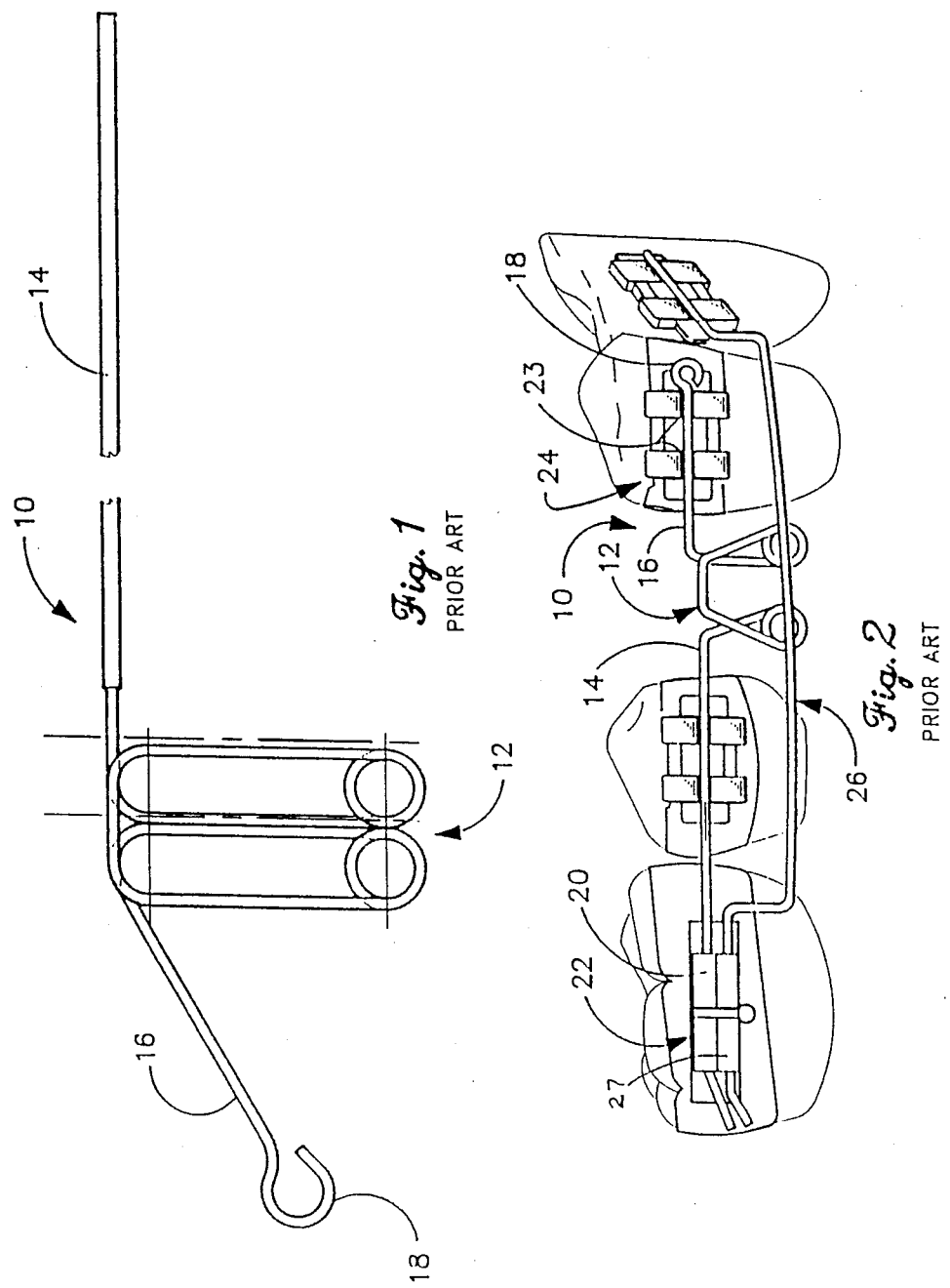

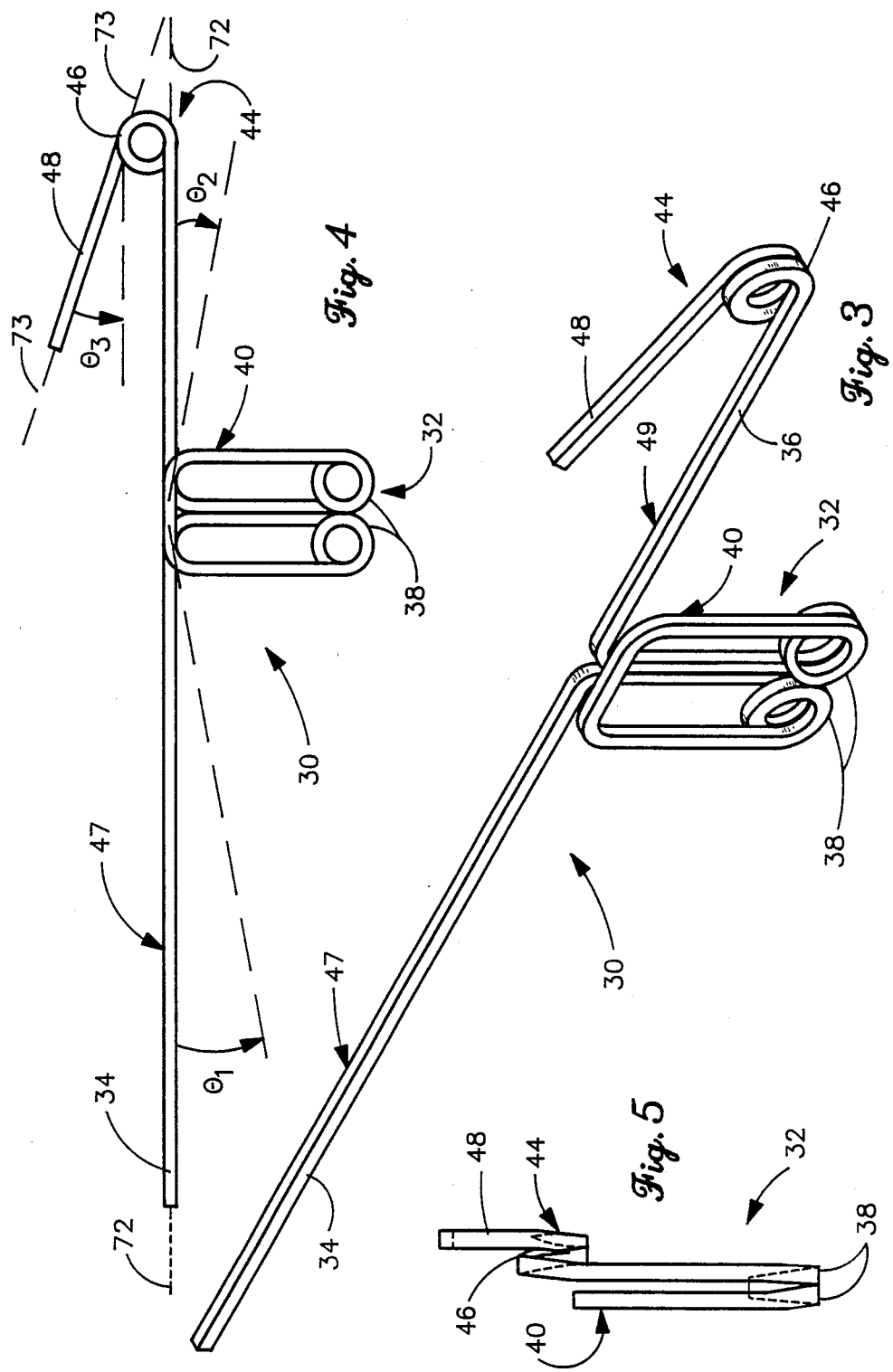

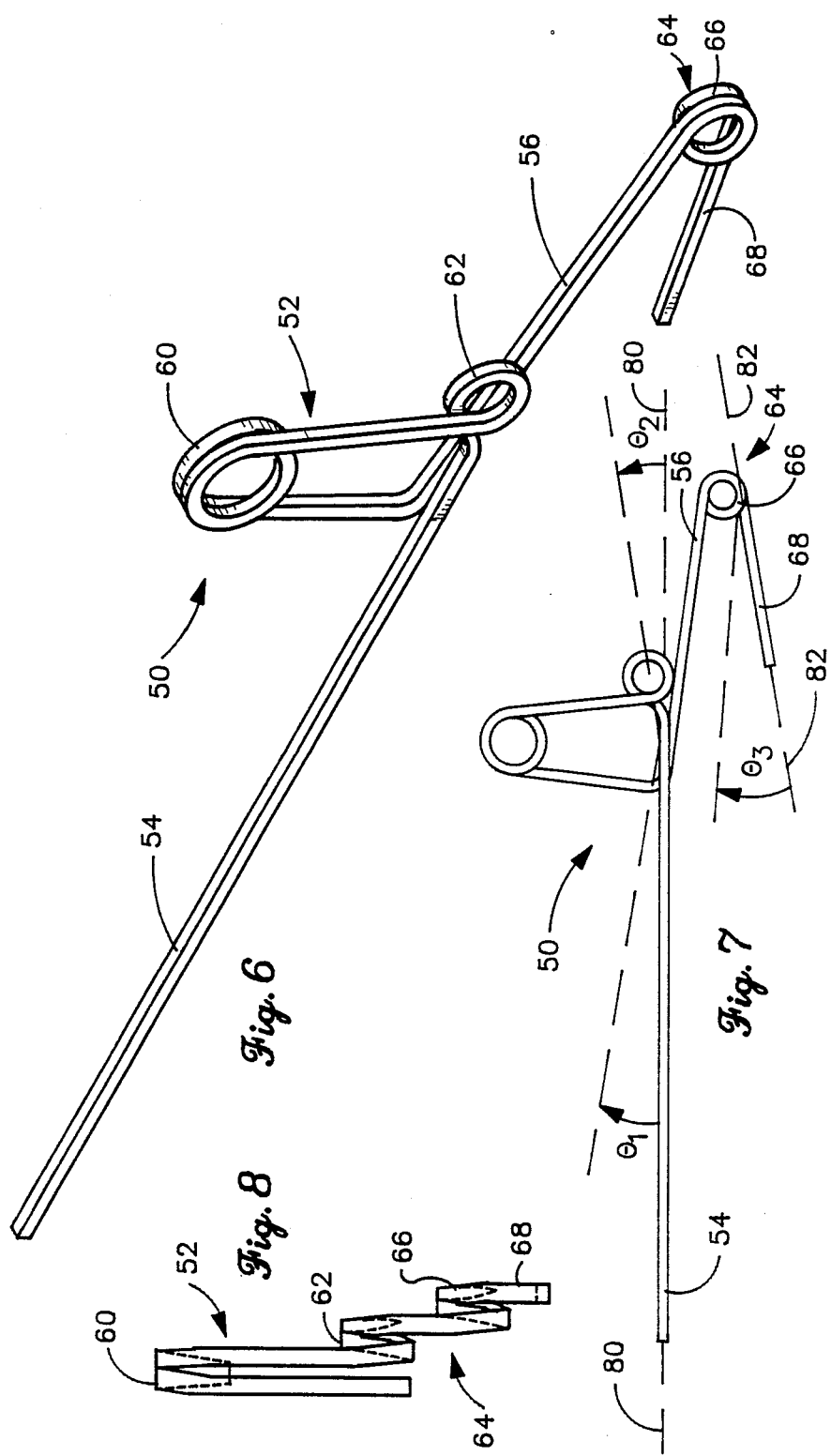

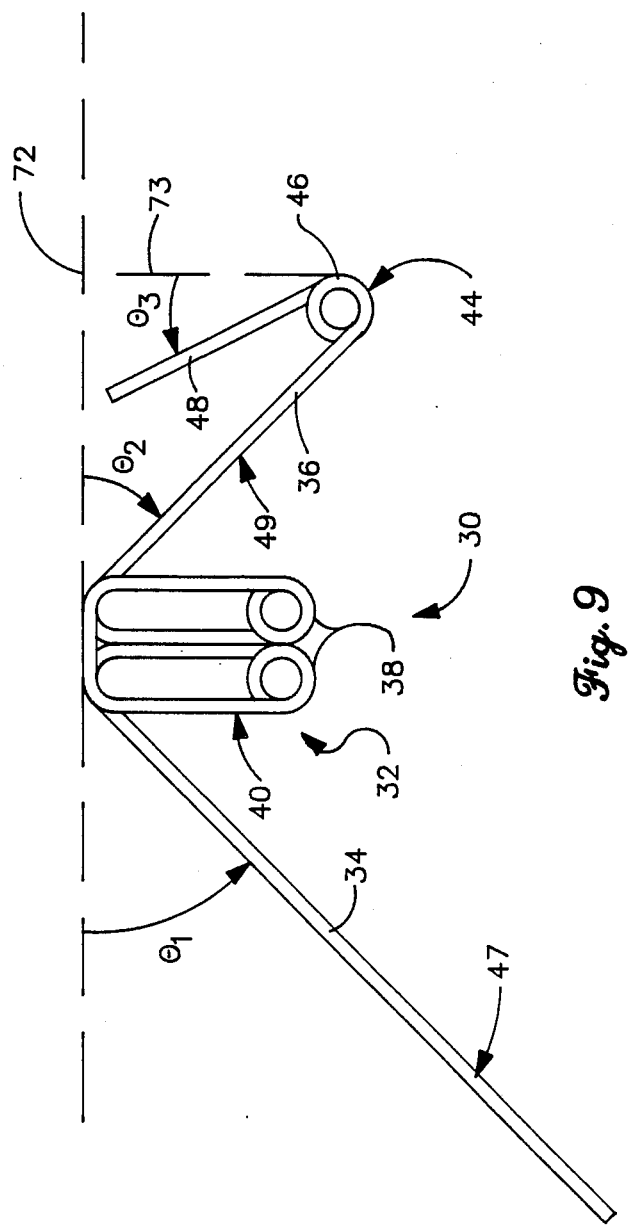

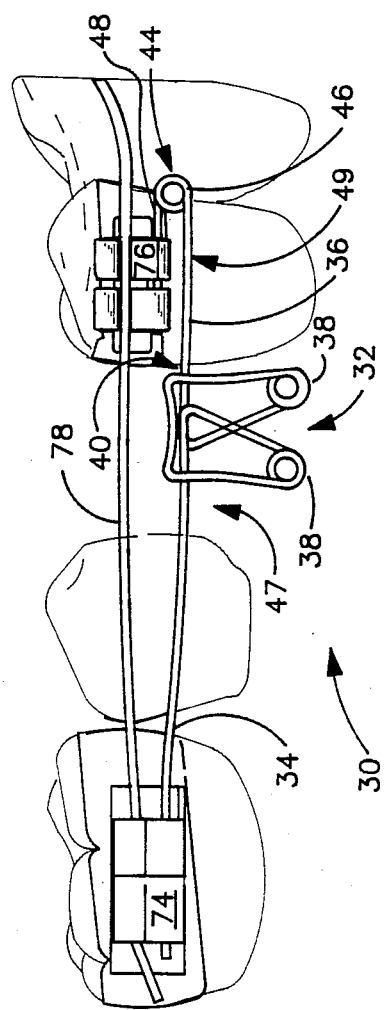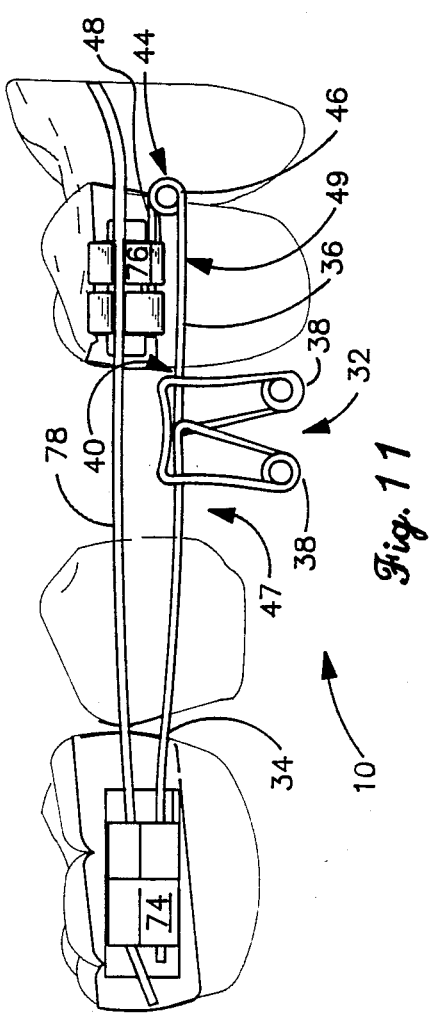

ORTHODONTIC APPLIANCE FOR REDUCING TOOTH ROTATION

FIELD OF THE INVENTION

The present invention relates to a method and apparatus for reducing the space between teeth while substantially reducing unwanted rotation, and more particularly, to an orthodontic appliance for preventing unwanted rotation of the tooth during its translational movement along a main guidewire.

BACKGROUND OF THE INVENTION

It is often desirable to correct tooth placement by employment of techniques facilitating space closure. Use of orthodontic appliances to control tooth movement during space closure is well known. Gaps may be reduced by reciprocal movement of teeth toward each other, or anterior retraction/posterior protraction of one or more teeth relative to one or more other teeth. Space closure is made difficult in that a simple force applied to a tooth may cause translation and/or rotation.

Under ideal conditions, a tooth can be translated through the alveolar crest, without unwanted rotation or tipping by applying a line of force at a tooth's center of resistance. Unfortunately, during space closure, forces are generally placed at a bracket which is typically positioned above the center of resistance. This generally produces a moment causing rotation of the tooth about a point somewhere between the root center of the tooth and its apex. It has been recognized that the movement resulting in tipping ($M_F$) can be counteracted by applying a counter-moment ($M_C$) More specifically, a couple is created which moves the "center of rotation" to infinity. Various "edgewise techniques," also known as "sliding mechanics," have been employed to provide for controlled tooth movements in which $M_F$ and $M_C$ are appropriately balanced. In one known technique, forces and moments are balanced by a centered "gable" placed in a main arch-wire, in combination with a force from an elastic or simple spring, to deliver a couple to overcome tipping during space closure. While a properly centered gable bend will produce equal and opposite moments of the roots, off-centered bends produce unequal moments which become further unbalanced as the gable bend is moved progressively away from the middle of the extraction site during space closure.

In another known technique, a squashed vertical loop with an edgewise wire, known as a "bull loop," is activated by opening the same the distance of a "thin dime". While bull loops can be effective in generating ideal "moment-to-force (M/F) ratios", they tend to be impractical since their range of activation is highly limited. Other edgewise techniques are discussed in Ricketts, R. *Features of the Bioprooressive Therapy* (No. 16) (1974) which is incorporated by reference.

"Segmented arch techniques," such as those promoted by J. Burstone, offer systems with controlled tooth movement and excellent M/F ratios, but contain numerous components which may be difficult to manipulate. Examples of orthodontic appliances of the segmented arch type may be found in Burstone U.S. Pat. No. 4,197,643. In using segmented arch techniques, no continous arch-wire is present between anterior and posterior segments of the teeth. Due to the elimination of the sliding resistance of the main arch, an overall reduction in force is realized. Without the presence of the arch-wire, however, nothing prevents anterior and posterior segments from leaving the occlusial plane due to errors in the M/F ratio between segments by unintentional or accidental means.

Other segmented arch techniques are discussed in the above-mentioned Ricketts reference. While the Ricketts cuspid retractors may be used with a utility arch, these cuspid retractors are believed not used with a main arch. Hence, the Ricketts system does not necessarily prevent unwanted rotation and particularly lacks the "fail-safe" approach of sliding mechanics. Moreover, the Ricketts appliance is gabled pursuant to insertion into brackets and, as mentioned above, the gable can become unbalanced as the gable bend is moved progressively away from the middle of the extraction site during space closure.

In view of the above-discussed prior art, there is a demand for a system that incorporates the theory of segmented arch techniques, which provide excellent M/F ratios, along with the fail-safe mechanism inherent to sliding mechanics. In view of the typical practitioner's reluctance to make drastic changes in orthodontic appliance systems, however, any proposed systems should be "user-friendly," i.e. adaptable for use with much of the armamentarium and appliances typically associated with either technique.

SUMMARY OF THE INVENTION

The present invention relates to an orthodontic appliance for preventing unwanted rotation of a tooth during its translational movement along a main guide-wire. The appliance is held by brackets affixed to teeth. The appliance includes a main spring assembly for causing, when activated, translational movement of a tooth along a main guide-wire to reduce the space between the tooth and another tooth. An auxiliary spring assembly, which is separate and spaced from the main spring assembly, includes a spring and a mesial leg extending from the spring. The mesial leg extends in a direction from the spring to a side of the bracket for connecting the mesial leg and the spring to the bracket.

In operation, the auxiliary spring assembly causes a counter-moment to the moment created during translational movement of the tooth in order to substantially reduce unwanted rotation of the tooth. Orthodontic wire interconnects the auxiliary spring assembly and the main spring assembly, and the interconnecting wire includes an anchor end to be connected to another tooth, other than the tooth having the bracket to which the auxiliary spring assembly is connected.

In one preferred embodiment of the invention, a first bracket having first and second slots is affixed to a first tooth. A second bracket, having at least a first slot, is affixed to a second tooth. A main guide-wire is positioned between the first and second spaced-apart teeth using the first slots of the first and second brackets. Prior to insertion of the orthodontic appliance into the brackets, the interconnecting wire and mesial leg of the auxiliary spring are bent to form at least three angles about a given reference plane. The mesial leg of the auxiliary spring is located in the second slot of the first bracket and the anchoring end of the retractor is affixed to one of the second tooth and another tooth by pulling and cinching the anchoring end.

A principal advantage of the present orthodontic appliance is that it provides for use of sliding mechanics in conjunction with segmented arch techniques. Accordingly, translation is optimally achieved and the possibility of unwanted rotation during translation is minimized. Of equal importance is that these benefits are gained without significant increases in componentry requirements and start-up investments. Hence the transition to the present system is reasonably achieved on a cost effective basis by practitioners who use either technique.

Another advantage is that the system affords highly accurate and precise control of M/F ratios and thus ensures the achievement of optimal translation. Employment of an auxiliary spring assembly allows for generation of a counter-moment which can be advantageously applied to balance a moment typically encountered during translation. Consequently, translation can be performed at highly efficient levels without fear of unintentionally promoting over-rotation. Moreover, maximized control of the M/F ratios results in cost reductions since the need to remedy unwanted tipping is alleviated.

Yet another advantage of the present invention lies in its compatibility with advanced quantitative analytical techniques. More specifically, due to its simple, yet functional design, the present retractor assembly is particularly amenable to computer modeling. Thus, operating parameters, such as optimal magnitudes of angles to be configured in the retractor assembly are achieved with the highest levels of accuracy and ease.

These and other features, advantages and objects of the present invention will be further understood and appreciated by those skilled in the art by reference to the following specification, claims and drawings appended hereto.

BRIEF DESCRIPTION OF THE DRAWINGS

FIG. 1 illustrates a prior art mandibular retractor assembly;

FIG. 2 illustrates the prior art mandibular retractor assembly connected to teeth for closing the space between the teeth;

FIG. 3 is a perspective view of a retractor assembly of the present invention;

FIG. 4 is a front plan view of the retractor assembly of FIG. 3;

FIG. 5 is a side plan view of the retractor assembly of FIG. 3;

FIG. 6 is a perspective view of another retractor assembly of the present invention;

FIG. 7 is a front plan view of the retractor assembly of FIG. 6;

FIG. 8 is a side plan view of the retractor assembly of FIG. 6;

FIG. 9 is a front plan view of the retractor of FIG. 3 configured for insertion into brackets mounted on two or more teeth;

FIG. 10 is a front-elevational, fragmentary view of the retractor of FIG. 9 at an extraction site prior to activation of the retractor;

FIG. 11 is a front-elevational, fragmentary view of the retractor of FIG. 9 at an extraction site, subsequent to activation of the retractor.

DETAILED DESCRIPTION OF THE PREFERRED EMBODIMENTS

For purposes of description herein, the terms "upper," "lower," "right," "left," "rear," "front," "vertical," "horizontal" and derivatives thereof shall relate to the invention as oriented in the drawings attached herewith. However, it is to be understood that the invention may assume various alternative orientations and step sequences, except where expressly specified to the contrary. It is also to be understood that the specific devices and processes illustrated in the attached drawings and described in the following specification, are simply exemplary embodiments of the inventive concepts defined in the appended claims. Hence, specific dimensions and other physical characteristics relating to the embodiments disclosed herein are not to be considered as limiting, unless the claims by their language, expressly state otherwise.

The reference numeral 10 (FIG. 1) generally designates a prior art mandibular retractor assembly typically employed on the right side of the arch during controlled tooth movement. Retractor assembly 10 comprises a double closed helix 12 operatively connected to a distal leg 14 and mesial leg 16. An anchoring member 18 is provided at an end of mesial leg 16. Prior to application of retractor 10, legs 14 and 16 are bent downwardly until a desired "gable" is achieved.

Distal leg 14 is inserted into a tube 20 (FIG. 2) of bracket 22, while mesial leg 16 is positioned in a slot 23 of a bracket 24 with anchoring member 18 proximate to a mesial side of bracket 24. Retractor assembly 10 is activated by pulling and cinching an end of distal leg 14. As distal leg 14 is pulled, mesial leg 16, along with anchoring member 18, is seated within bracket 24. As further illustrated in FIG. 2, a utility arch 26 is used along with retractor assembly 10. As is conventional, utility arch 26, which is secured to tube 27 of bracket 22 and another tube (not shown) along the arch, served as anchorage between posterior and anterior teeth. The utility arch 26 does not, however, serve to prevent over-rotation of teeth during translation of the same. The retractor assembly 10 is constructed for use in the mandibule, and the design of retractor assembly would vary somewhat when used in the maxillum. As will be appreciated by those skilled in the art, however, the concepts employed to effect controlled tooth movement with retractor assembly 10 is basically the same for both the mandibule and maxillum.

The reference numeral 30 (FIGS. 3–5) generally designates one of the retractor assemblies embodying the present invention. The mandibular retractor assembly 30, which is employed for tooth movement in the mandibule, comprises a main spring 32 interconnected with a distal leg 34 and the first or main spring mesial leg 36. In the present example, main spring 32 comprises a double closed helix having two helixes 38 interconnected with legs 34 and 36 as well as a yoke 40. An auxiliary spring assembly 44 is operatively connected to one end of first mesial leg 36. In the preferred embodiment, auxiliary spring 44 includes a closed helix 46 interconnected with first mesial leg 36 and a second or auxiliary mesial leg 48. A posterior end section 47 of the retractor assembly 30 is defined by the distal leg 34, while an anterior end section 49 is defined by the first mesial leg 36 and the auxiliary spring assembly 44. Additionally, mandibular retractor assembly 30 is constructed of a stainless steel alloy. Of course other materials could be used for construction without materially changing the function of the mandibular retractor assembly 30.

As explained in further detail below, it is advantageous to adapt mandibular retractor assembly 30 for specific use along the left side or the right side of the arch. In the preferred embodiment, main spring 32 and auxiliary spring 44 are oriented according to whether retractor 30 is to be used on the left side or right side of the arch. Mandibular retractor assembly 30 is typically oriented in the mouth so that second mesial leg 48 faces lingually and yoke 40 faces buccally. In the present example, the mandibular retractor assembly 30 of FIGS. 3–5 is employed on the arch right side. As can be appreciated by those skilled in the art, simple rearrangement of the components of mandibular retractor assembly 30 allows for achievement of the above constraints with respect to main spring 32 and second mesial leg 48 for the left side of the arch. That is, construction of a left side mandibular assembly could be achieved by simply rotating helixes 38 so that yoke 40 faces buccally when the left side retractor is positioned along the left side of the arch.

The reference numeral 50 (FIGS. 6–8) generally designates another retractor assembly embodying the present invention. The retractor assembly 50, which is used for tooth movement in the maxillum, comprises main spring 52 interconnected with a distal leg 54 and a first or main spring mesial leg 56. Main spring 52 includes two single closed helixes 60 and 62, the latter of which is preferably disposed proximate to first mesial leg 56. An auxiliary spring mechanism 64 is provided along an end of first mesial leg 56. As with auxiliary spring 44, auxiliary spring 64 includes a helix 66 interconnected with both the first mesial leg 56 and a second or auxiliary mesial leg 68. In the preferred embodiment, maxillary retractor assembly 50 is constructed of stainless steel alloy. Of course, other materials could be used for construction without materially changing the function of maxillary retractor assembly 50.

As with mandibular retraction assembly 30, the left side equivalent of maxillary retraction assembly 50 can be achieved by a simple rearrangement of the components of maxillary retractor assembly 50. In the preferred embodiments, second mesial leg 68 faces lingually, during operation, whether maxillary retraction assembly 50 is positioned along the left side or the right side of the arch.

Referring now to FIGS. 9–11, the operation of mandibular retractor assembly 30 will be set forth in detail. While operation is only described for those retractor assemblies 30 and 50 used on the right side of the arch, it should be understood that the following description is applicable for retractor assemblies 30 and 50 used on the left side of the arch. Prior to applying mandibular retractor assembly 30 in the mouth (FIGS. 4 and 9), distal leg 34, first mesial leg 36 and second mesial leg 48 are bent to form angles theta 1, theta 2 and theta 3, respectively. As illustrated in FIGS. 4 and 9, angles theta 1 and theta 2 are defined relative to reference plane 72, while angle theta 3 is defined relative to reference plane 73. The magnitudes of theta 1, theta 2 and theta 3 are set according to the space closure technique desired to control tooth movement. One of three space closure techniques is typically used, namely anterior retraction, reciprocal attraction or posterior protraction. Performance of one of these three space closure techniques is achieved by appropriate adjustment of theta 1, theta 2 and theta 3.

A finite element model was created from a general purpose finite element package to determine optimum magnitudes for the angles of theta 1, theta 2 and theta 3 used in each of the above-mentioned techniques. As a result of such computer modeling, it was found that the three techniques could be effectively achieved through using the following guidelines for adjustment of angle magnitudes:

| Technique | Theta 1 | Theta 2 | Theta 3 |
| --- | --- | --- | --- |
| Anterior Retraction | 45° | 45° | 0° |
| Reciprocal Attraction | 45° | 45° | 15° |
| Posterior Retraction | 45° | 45° | 30° |

It should be appreciated that the above angle magnitudes are merely suggested guidelines and by no means represent critical values. In actual fact, there are many combinations of theta 1, theta 2 and theta 3 that would suffice to provide highly adequate levels of controlled tooth movement. As explained in further detail below, any combination of theta 1, theta 2 and theta 3 can be employed to effect controlled tooth movement as long as appropriate alpha (anterior) and beta (posterior) M/F ratios are maintained during deactivation.

As best illustrated in FIG. 10, after setting the magnitudes for theta 1, theta 2 and theta 3, distal leg 34 and second mesial leg 48 are inserted into the mesial ends of brackets 74 and 76, respectively. Experimentation indicates that controlled tooth movement is optimized when mandibular retractor assembly 30 is secured at the mesial ends of brackets 74 and 76. This relationship holds true whether controlled tooth movement is performed on the right arch side or the left arch side. As suggested above, the construction of mandibular retractor assembly 30 must be slightly altered in order to achieve connection at the mesial ends on the left arch side.

In one example, brackets 74 and 76 are a gingival auxiliary tube and a modified cuspid bracket, respectively. As will be appreciated by those skilled in the art, however, other brackets, depending on the type of tooth movement desired, could be employed without significantly affecting the purpose for which the invention was intended. In the preferred embodiment, brackets 74 and 76 are adapted to receive a main arch-wire 78 (FIGS. 10 and 11) which, provides a highly advantageous "fail-safe" system. That is, the system is self-limiting because teeth are translated along main arch-wire 78 such that tooth movements fall within limitations defined by the interface between arch-wire 78 and brackets 74 and 76. A primary purpose of arch-wire 78 is to prevent anterior and posterior segments from leaving the occlusal plane due to errors in the M/F ratio between segments. As mentioned above, this is in contradistinction to segmental arch techniques which generally reject the concept of sliding mechanics for space closure.

The second mesial leg 48 is anchored into place within bracket 74 (FIG. 11) as retraction assembly 30 is "activated." Activation is effected by pulling an end of distal leg 34 a desired distance and cinching the same at bracket 74. Applicants have found that activation is optimized by pulling the end of distal leg 34 approximately 2 mm. As should be appreciated, over a period of time, typically a period of about 3–6 weeks, mandibular retraction assembly 30 is deactivated and the activation distance decreases from 2 mm to 0 mm. Even after the horizontal activation of mandibular retraction assembly 30 is finally expended, it continues to operate as a root spring, causing increases in the M/F ratios. After deactivation, to continue the controlled tooth movement process, it is necessary to reactivate mandibular retraction assembly 30.

As already stressed above, a given technique of controlled tooth movement is facilitated by proper choice of angle magnitudes for theta 1, theta 2 and theta 3. The importance of angle selection is best illustrated by reference to Tables 1-3, which are generated by computer modeling and show the results of activation for three space closure techniques used with the mandibular retraction assembly 30. For the three cases of Tables 1-3, respectively, theta 1 and theta 2 are held constant at 45° while theta 3 is varied from 0° to 30°. The results of Tables 1-3, include values, representing horizontal and vertical forces as well as anterior (alpha) and posterior (beta) moments, measured for each activation period. For a given activation distance, such as 2 mm, with theta 1 and theta 2 held constant, as theta 3 is increased from 0° to 30°, alpha M/F ratios increase as beta M/F ratios decrease.

As should be evident from the results of Tables 1-3, one of three techniques can readily be achieved by simply varying theta 3 as theta 1 and theta 2 are held constant. It should be appreciated that auxiliary spring mechanism 44 can be advantageously used to provide high levels of control. As demonstrated by the results of Tables 1-3, alpha and beta M/F ratios can be varied as a direct function of the adjustment of second mesial leg 48 as the magnitudes of theta 1 and theta 2 are held constant. Essentially such adjustment allows for offsetting of the moment generated by the beta portion of mandibular retraction assembly 30 against the moment generated by the corresponding alpha portion. Experience indicates that segmental arch techniques, in which only theta 1 and theta 2 are typically employed, simply cannot provide the sort of high-precision control of M/F ratios which is made available through the use of retraction assembly 30 with its auxiliary spring assembly 44.

TABLE 1

MANDIBULAR RETRACTION SPRING (45_45_00) MAXIMUM ANTERIOR RETRACTION

| ACTIVATION (mm) | HOR FORCE (gm) | VERT FORCE (gm) | ALPHA MOMENT (gm*mm) | BETA MOMENT (gm*mm) | SPRING RATE (gm/mm) | ALPHA M/F (mm) | BETA M/F (mm) |
|---|---|---|---|---|---|---|---|
| 0.0 | 0 | 86 | 724 | 2316 | | | |
| 0.5 | 115 | 94 | 904 | 2460 | 229.3 | 7.9 | 21.5 |
| 1.0 | 230 | 101 | 1076 | 2583 | 229.5 | 4.7 | 11.3 |
| 1.5 | 344 | 106 | 1243 | 2687 | 229.6 | 3.6 | 7.8 |
| 2.0 | 459 | 112 | 1404 | 2776 | 229.7 | 3.1 | 6.0 |
| 2.5 | 574 | 116 | 1562 | 2852 | 229.8 | 2.7 | 5.0 |
| 3.0 | 690 | 120 | 1717 | 2915 | 229.9 | 2.5 | 4.2 |
| 3.5 | 805 | 123 | 1870 | 2967 | 230.1 | 2.3 | 3.7 |
| 4.0 | 921 | 126 | 2020 | 3010 | 230.3 | 2.2 | 3.3 |

TABLE 2

MANDIBULAR RETRACTION SPRING (45_45_15) MAXIMUM RECIRPROCAL ATTRACTION

| ACTIVATION (mm) | HOR FORCE (gm) | VERT FORCE (gm) | ALPHA MOMENT (gm*mm) | BETA MOMENT (gm*mm) | SPRING RATE (gm/mm) | ALPHA M/F (mm) | BETA M/F (mm) |
|---|---|---|---|---|---|---|---|
| 0.0 | 0 | 10 | 1458 | 1653 | | | |
| 0.5 | 110 | 21 | 1657 | 1840 | 221.7 | 15.0 | 16.6 |
| 1.0 | 222 | 31 | 1848 | 2002 | 222.4 | 8.3 | 9.0 |
| 1.5 | 334 | 39 | 2032 | 2143 | 223.0 | 6.1 | 6.4 |
| 2.0 | 447 | 47 | 2210 | 2265 | 223.6 | 4.9 | 5.1 |
| 2.5 | 560 | 53 | 2384 | 2371 | 224.0 | 4.3 | 4.2 |
| 3.0 | 673 | 59 | 2553 | 2463 | 224.5 | 3.8 | 3.7 |
| 3.5 | 787 | 64 | 2720 | 2541 | 224.9 | 3.5 | 3.2 |
| 4.0 | 901 | 68 | 2884 | 2607 | 225.4 | 3.2 | 2.9 |

TABLE 3

MANDIBULAR RETRACTION SPRING (45_45_30) MAXIMUM POSTERIOR PROTRACTION

| ACTIVATION (mm) | HOR FORCE (gm) | VERT FORCE (gm) | ALPHA MOMENT (gm*mm) | BETA MOMENT (gm*mm) | SPRING RATE (gm/mm) | ALPHA M/F (mm) | BETA M/F (mm) |
|---|---|---|---|---|---|---|---|
| 0.0 | 0 | −64 | 2142 | 1004 | | | |
| 0.5 | 107 | −50 | 2356 | 1230 | 212.3 | 22.2 | 11.6 |
| 1.0 | 214 | −38 | 2562 | 1430 | 213.7 | 12.0 | 6.7 |
| 1.5 | 322 | −26 | 2760 | 1607 | 214.9 | 8.6 | 5.0 |
| 2.0 | 432 | −16 | 2951 | 1762 | 215.9 | 6.8 | 4.1 |
| 2.5 | 542 | −8 | 3137 | 1899 | 216.9 | 5.8 | 3.5 |
| 3.0 | 653 | 0 | 3318 | 2018 | 217.7 | 5.1 | 3.1 |
| 3.5 | 765 | 7 | 3495 | 2123 | 218.5 | 4.6 | 2.8 |
| 4.0 | 877 | 14 | 3669 | 2214 | 219.3 | 4.2 | 2.5 |

Conversely, for the same activation distance, with theta 1 and theta 2 held constant, as theta 3 is decreased from 30° to 0°, alpha M/F ratios decrease as beta M/F ratios increase.

The results of Tables 1-3, are particularly useful for analysis of M/F ratios during deactivation of mandibular retraction assembly 30. For example, examination of Table 2 shows nearly 450 grams of horizontal force with approximately a 2200 gm-mm moment for both posterior and anterior sections of retraction assembly 30. At 2 mm of activation, the M/F ratios are approximately 5 and increase to approximately 9 at 1 mm of remaining activation. Even after the horizontal activation of mandibular retraction assembly 30 is finally expended, it continues to operate as a root spring, increasing the M/F ratios to 16 and above.

Operation of maxillary retractor 50 is conceptually equivalent to that of mandibular retraction assembly 30 and will not be discussed in any considerable detail herein. It is noteworthy, however, that in contrast to retraction assembly 30, distal leg 54 and first mesial leg 56 (FIGS. 6 and 7) are bent upward, rather than downward, prior to application. As illustrated in FIG. 7, corresponding angles theta 1 and theta 2 for maxillary retractor 50 are measured relative to reference plane 80 while theta 3 is measured relative to reference plane 82. As with retraction assembly 30, maxillary auxiliary retractor 50 provides a system in which M/F ratios can be precisely and accurately controlled. The following guidelines are recommended for operation of maxillary retractor 50:

| Technique | Theta 1 | Theta 2 | Theta 3 |
| --- | --- | --- | --- |
| Anterior Retraction | 45° | 45° | 15° |
| Reciprocal Attraction | 45° | 45° | 30° |
| Posterior Retraction | 45° | 45° | 45° |

Due to the construction of the above-described retractor assemblies, they are easy to manufacture and use. In view of their simple, yet functional design they are readily adapted for use in preexisting systems employing sliding mechanics or segmental arch techniques. Moreover, use of the retractor assemblies with a main arch-wire promotes safety, specifically ensuring that the teeth, during translation, are maintained within the occlusial plane. Since the retractor assemblies are capable of highly precise levels of M/F ratio control, the problems associated with unwanted rotation are alleviated, so that translation of teeth is optimized.

In the foregoing description, it will be readily appreciated by those skilled in the art that modifications may be made to the invention without departing from the concepts disclosed herein. Such modifications are to be considered as included in the following claims, unless these claims by their language expressly state otherwise.

The embodiments of the invention in which an exclusive property or privilege is claimed are defined as follows:

1. A method for reducing the space between teeth while substantially reducing unwanted rotation of a tooth being moved, comprising:
   affixing a first bracket having first and second slots to a first tooth;
   affixing a second bracket having at least a first slot to a second tooth;
   positioning a main guide wire between the first and second spaced apart teeth using said first bracket slots of said first and second brackets;
   providing an orthodontic appliance having a main spring, an anterior end section and an anchoring end;
   securing a part of said anterior end section to said second slot of said first bracket;
   affixing said anchoring end of said orthodontic appliance to one of the second tooth and another tooth;
   activating said main spring;
   permitting translational movement of the first tooth along said main guide wire while substantially preventing rotation of the first tooth using portions of said anterior end section; and
   using said main guide wire as a safeguard to substantially prevent unwanted rotation of the first tooth beyond a certain amount of rotation.

2. The method of claim 1, wherein:
   said anterior end section portions include an auxiliary spring means that has a spring and an auxiliary mesial leg and wherein said anterior end section is secured to said second slot by locating said auxiliary mesial leg in said second slot.

3. The method of claim 2, wherein:
   said auxiliary mesial leg is inserted into a mesial side of said second slot of said first bracket.

4. The method of claim 2, wherein said anterior end section includes a mesial leg and said anchoring end, said anterior end section mesial leg and said auxiliary mesial leg are bendable relative to one of a first reference plane and a second reference plane and the method further comprises the steps of:
   bending said anchoring end wherein a first angle is formed between said anchoring end and the first reference plane;
   bending said anterior end section mesial leg wherein a second angle is formed between said anterior end section mesial leg and the first reference plane; and
   bending said auxiliary mesial leg wherein a third angle is formed between said auxiliary mesial leg and the second reference plane.

5. The method of claim 4, wherein:
   one of anterior retraction, reciprocal attraction and posterior protraction is achieved by altering the magnitude of the third angle while holding the magnitudes of the first and second angles constant.

6. The method of claim 1, wherein said step of activating includes:
   pulling said anchoring end a predetermined activation distance prior to affixing said anchoring end to one of the second tooth and another tooth.

7. The method of claim 6, wherein:
   said predetermined activation distance is about 2 mm.

8. An orthodontic system for preventing unwanted rotation of a tooth during its translational movement in reducing a space between teeth, comprising:
   a first bracket having first and second slots and adapted to be affixed to a first tooth;
   a second bracket having at least a first slot and adapted to be affixed to a second tooth;
   a main guide wire being received by said first slot of said first and second bracket and extending between the first and second teeth, said guide wire inhibiting movement of the first tooth out of an occlusal plane; and
   an orthodontic assembly operating independently or any guide wire including said main guide wire for substantially reducing unwanted rotation of the first tooth during its translation movement, comprising:
      said spring means for causing, when activated, a translational movement of the first tooth in a direction along said main guide wire to reduce the space between the first tooth and another tooth, and
      orthodontic wire means operatively associated with said main spring means, said wire means including an anchoring end connected to one of the second tooth and another tooth and an anterior end section operatively connected to said second slot of said first bracket, wherein said anterior end section is constructed and arranged to adjustably reduce rotation of the first tooth by applying a countermoment to offset a moment created during its translational movement.

9. An orthodontic system for preventing unwanted rotation of a tooth during its translational movement in reducing a space between teeth, comprising:
a first bracket having first and second slots and adapted to be fixed to a second tooth;
a second bracket having at least a first slot and adapted to be affixed to a second tooth;
a main guide wire being received by said first slots of said first and second brackets and extending between the first and second teeth; and
an orthodontic assembly for substantially reducing unwanted rotation of the first tooth during its translational movement, comprising:
main spring means for causing, when activated, a translational movement of the first tooth along said main guide wire to reduce the space between the first tooth and another tooth, and
orthodontic wire means operatively associated with said main spring means, said wire means including an anchoring end connected to one of the second tooth and another tooth and an anterior end section operatively connected to said second slot of said first bracket, wherein said anterior end section includes means for reducing rotation of the first tooth during its translational movement, said means for reducing rotation includes auxiliary spring means including a spring and a mesial leg extending from said spring, wherein said auxiliary mesial leg extends in a direction from said spring to a side of said first bracket and is received by said second slot of said first bracket for connecting said spring and said auxiliary mesial leg to said first bracket, wherein said auxiliary spring means causes a countermoment to the moment created during translational movement of the first tooth in order to reduce rotation of the first tooth.

10. The apparatus of claim 9, wherein:
said auxiliary mesial leg extends to a mesial side of said first bracket for connecting said spring and said mesial leg to the mesial side of said first bracket.

11. The apparatus of claim 9, wherein:
said orthodontic wire means is adapted to be bent to form first and second angles relative to a first reference plane; and said auxiliary mesial leg is adapted to be bent to form a third angle relative to a second reference plane 12. The apparatus of claim 9, wherein:
said orthodontic assembly is adapted for use in a mandibular section wherein said auxiliary spring means is positioned above a substantial portion of said main spring when said orthodontic wire means is substantially straightened.

13. The apparatus of claim 9, wherein:
said orthodontic assembly is adapted for use in a maxillary section wherein said auxiliary spring means is positioned below a substantial portion of said main spring when said orthodontic wire means is substantially straightened.

14. An orthodontic appliance for preventing unwanted rotation of a tooth during its translational movement along a main guide wire, said appliance being adapted to be held by at least one bracket affixed to a tooth and comprising:
main spring means for causing, when activated, translational movement of the tooth along the main guide wire to reduce the space between the tooth and another tooth;
auxiliary spring means, separate and spaced from said main spring means, said auxiliary spring means including a spring and a mesial leg extending from said spring, wherein said mesial leg extends in a direction from said spring to a side of the bracket for connecting said mesial leg and spring to the bracket and wherein said auxiliary spring means causes a counter moment to the moment created during translational movement of the tooth in order to substantially reduce unwanted rotation of the tooth; and
orthodontic wire means interconnecting said auxiliary spring means and said main spring means, said wire means including an anchoring end adapted to be connected to another tooth other than the tooth having the bracket to which said auxiliary spring means is connected.

15. The orthodontic appliance of claim 14, wherein:
said mesial leg of said auxiliary spring extends to and is adapted to be connected at a mesial side of the bracket.

16. The orthodontic appliance of claim 14, wherein:
said main spring means includes at least two closed helixes positioned adjacent one another.

17. The orthodontic appliance of claim 14, wherein:
said auxiliary spring means includes at least one closed helix.

18. The orthodontic appliance of claim 14, wherein:
said orthodontic wire means is adapted to be bent to form first and second angles relative to a first reference plane; and
said mesial leg is adapted to be bent to form a third angle relative to a second reference plane.

* * * * *